United States Patent
Da Silva Macedo, Jr.

(10) Patent No.: US 7,943,811 B2
(45) Date of Patent: May 17, 2011

(54) ADHESIVE BANDAGE AND A PROCESS FOR MANUFACTURING AN ADHESIVE BANDAGE

(75) Inventor: Carlos Da Silva Macedo, Jr., São José dos Campos, SP (BR)

(73) Assignee: Johnson & Johnson Industrial Ltda. (BR)

( * ) Notice: Subject to any disclaimer, the term of this patent is extended or adjusted under 35 U.S.C. 154(b) by 77 days.

(21) Appl. No.: 11/877,794

(22) Filed: Oct. 24, 2007

(65) Prior Publication Data

US 2009/0112142 A1    Apr. 30, 2009

(51) Int. Cl.
*A61F 13/00* (2006.01)
(52) U.S. Cl. .............. 602/54; 602/42; 602/47; 602/56
(58) Field of Classification Search ............ 602/41–43, 602/45–48, 52, 54–56
See application file for complete search history.

(56) References Cited

U.S. PATENT DOCUMENTS

| | | | |
|---|---|---|---|
| 4,538,603 A * | 9/1985 | Pawelchak et al. ............ 602/56 |
| 4,622,089 A | 11/1986 | Lauritzen | |
| 5,250,043 A | 10/1993 | Castellana et al. | |
| 5,486,158 A | 1/1996 | Samuelsen | |
| 5,569,207 A | 10/1996 | Gisselberg et al. | |
| 5,643,187 A | 7/1997 | Naestoft et al. | |
| 5,681,579 A | 10/1997 | Freeman | |
| 6,207,875 B1 * | 3/2001 | Lindqvist et al. ............ 602/46 |
| 6,558,792 B1 | 5/2003 | Vaabengaard et al. | |
| 6,566,575 B1 | 5/2003 | Stickels et al. | |
| 2003/0199800 A1 * | 10/2003 | Levin ........................ 602/43 |
| 2004/0127835 A1 * | 7/2004 | Sigurjonsson et al. ......... 602/41 |
| 2005/0182347 A1 * | 8/2005 | Bishop et al. .................. 602/43 |
| 2007/0078365 A1 | 4/2007 | Macedo | |

FOREIGN PATENT DOCUMENTS

| | | |
|---|---|---|
| CA | 2 524 650 A | 4/2006 |
| EP | 0 275 353 B1 | 7/1988 |
| EP | 0 413 251 A | 2/1991 |
| EP | 0 768 071 B1 | 4/1997 |
| FR | 2 736 833 A | 1/1997 |
| WO | WO 03/057485 A | 7/2003 |
| WO | WO 2004/112852 A | 12/2004 |

* cited by examiner

*Primary Examiner* — Patricia M Bianco
*Assistant Examiner* — Keri J Nelson

(57) ABSTRACT

An adhesive bandage having a support layer with a first surface facing the skin of the user and which defines a first surface area, at least one first composite layer having an adhesive element applied to the first surface and substantially covering the whole of the first surface area, and at least one multi-layer system associated to at least a section of the first composite layer. The multi-layer system includes at least one permeable polymeric film layer and at least one second composite layer having at least one adhesive element and at least one hydrocolloidal element. The multi-layer system is associated to the first composite layer via the second composite layer or the permeable polymeric film layer.

9 Claims, 3 Drawing Sheets

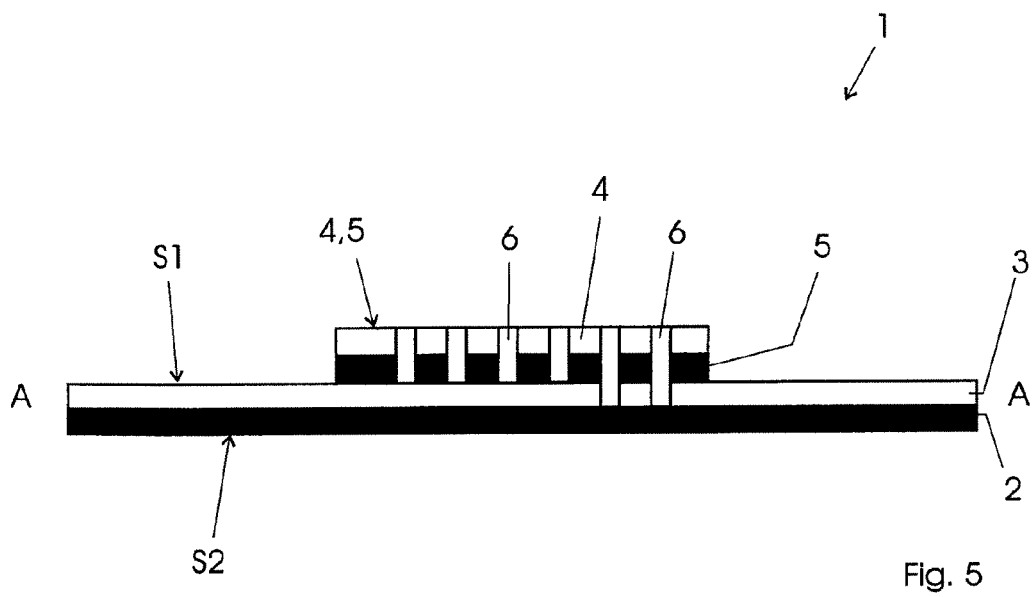
Fig. 5
PRIOR ART
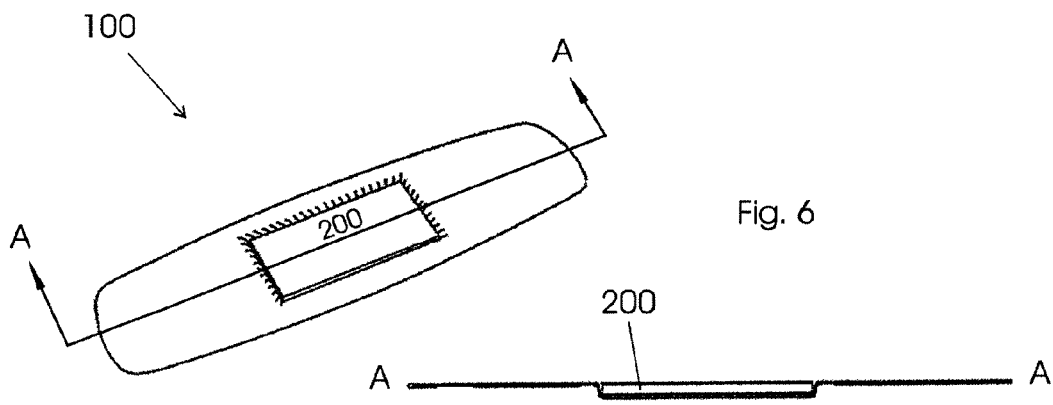
Fig. 6
Fig. 7

ADHESIVE BANDAGE AND A PROCESS FOR MANUFACTURING AN ADHESIVE BANDAGE

The present invention relates to an adhesive bandage to be applied specially to the skin, particularly an adhesive bandage that has great flexibility of use after having been applied to the skin, without, however, causing any damage to the injury upon removal and/or that has good absorption capacity for absorbing body exudates and provides good respirability. The invention further relates to a process for manufacturing this adhesive bandage.

DESCRIPTION OF THE PRIOR ART

Conventionally, adhesive bandages developed to be used on the skin, protecting it against injuries, or protecting the wounds from dirtiness, thus guaranteeing the efficacy of medicaments applied topically, comprise at least one film of a liquid-impermeable material, which prevents contamination of the wound as well.

At least one pad comprising at least one absorbent material and at least one adhesive element to attach the adhesive bandage to the skin is associated to the film. Preferably, the region intended for contact with the wound (the pad) does not have any adhesive, since the presence thereof might cause maceration in the injury upon removal and/or replacement of the adhesive bandage, which should be avoided so that the healing of the would can take place as rapidly as possible.

The acceleration of the healing is further enhanced by virtue of the fact that the film is permeable to gas and may optionally contain a plurality of through bores.

With a view to increase more and more the efficiency and comfort provided by a adhesive bandage, various improvements in this basic concept of adhesive bandage, which per se is extremely efficient, have been developed, as for example, improvement of the materials employed (more flexible, comfortable, cheap, with greater liquid-absorption capacity, etc.) or constitution of the bandage so as to prevent maceration/re-injury of the injury.

The first type of improved adhesive bandage is described in U.S. Pat. No. 5,569,207 and is provided with at least one opening for positioning a catheter, needle or the like. This bandage is ultimately devised for use on patients who are using catheters or needles, and comprises essentially a layer of hydrocolloid material facing the wound, an intermediate layer of an absorbent foam for retaining body exudates and an outer film that is permeable to gases but impermeable to liquids and to penetration by bacteria.

A second type of hydrocolloid bandage is described in document EP 0 768 071 and has a thin layer of a mixture of hydrocolloid product and adhesive, which is provided on one side with a flexible and transparent backing layer and, on the other side, with one of more removable sheets, which enables one to secure it to the injured skin. This bandage further has a number of linear depressions that serve as guides for its positioning and possible bending, according to the needs to use it. In this type of bandage, the adhesive protecting sheets are not flexible, so that it can only be deformed after removal of these sheets, that is to say, only at the moment of using it.

A third type of improved adhesive bandage is described in U.S. Pat. No. 5,250,043 and comprises essentially an adhesive layer, a pad of a superabsorbent element, a porous cover for this pad and a protective sheet. The pad cover comprises a plurality of orifices (openings) that enable body exudates to pass through and enhance the performance of the product.

A fourth type of hydrocolloid bandage is described in document EP 0 275 353 and comprises a perforated elastomeric film. This perforated polymeric film not only provides excellent properties of adhesion to the skin of the user, but also can be removed easily and with minimum re-injury.

A fifth type of improved adhesive bandage is described in U.S. Pat. No. 5,486,158 and comprises a first layer constituted by a removable protective film, a second layer constituted by a high-absorption component including colloid and, finally, a third layer that is an impermeable cover sheet. A plurality of grooves is arranged circumferentially.

Adhesive bandages composed by a single liquid-permeable and gas-permeable film constitute another development of this type of product and are extremely thinner, comfortable and discreet, since they do not have any type of pad or similar absorbent element. In order for this type of bandage to absorb the body exudates, the adhesive layer contains in its composition at least one hydrocolloid compound, which absorbs emanated fluid to saturation.

The flexibility resulting from the thin thickness of the adhesive bandages composed by a single film cause them to be adhered to the skin for a long time, even when the injury is located in body-articulation regions, so that the replacement thereof is necessary after saturation of the absorbent capacity of the hydrocolloid. As a result, in addition to the discreetness and comfort, the number of adhesive bandages used until recovery of a skin injury is reduced, decreasing the expenditures of the user with the product.

The description of this type of adhesive bandage is great because, beyond reduced thickness, it is possible to configure the film in a way that it masks the existence of the bandage or makes it transparent, being just a little noted when in use.

In opposition to the advantages commented on above, the great disadvantage of the single-layer adhesive bandages is their high adhesion to the wound, which causes maceration /re-injury upon removal thereof for replacement after saturation. This is due to the impossibility of controlling the rate or intensity of adhesion of an adhesive bandage to the wound, since it is composed exclusively of this film having adhesive with hydrocolloid.

Until the present moment an adhesive bandage had not been developed, particularly designed for being used as a dressing, which could join the best of conventional bandages provided with a pad (high absorption capacity, high respirability and good maceration/re-injury properties) with the advantages of single-film bandages, which are reduces thickness brining comfort and discreetness for the user.

OBJECTIVES OF THE INVENTION

An objective of the present invention is to provide an adhesive bandage for use on skin injuries, which has the characteristics of high peripheral-adhesion and absorption capability and, at the same time, provides comfort and discreetness for the user and has a good performance as far as maceration/re-injury of the wound, is concerned.

Also, the present invention has the objective of providing a process for manufacturing the aimed-at adhesive bandage.

BRIEF DESCRIPTION OF THE INVENTION

The objectives of the present invention are achieved by means of an adhesive bandage, particularly for use on the skin, comprising a polymeric film that has a first surface facing the skin of the user and a second opposite surface, the first surface defining a first surface area that receives the application of at least one first composite layer formed by at least one adhesive element and at least one hydrocolloid element, at least one segment of perforated polymeric film being associated to the composite layer applied to the first area, the segment of polymeric film having a second area substantially smaller than the first one.

Also, the objectives of the present invention are achieved by means of an adhesive bandage, particularly for use on the skin, comprising a polymeric film that has a first surface facing the skin of the user and a second opposite surface, the first surface defining a first surface area that receives the application of at least one first composite layer formed by at least one adhesive element and at least one hydrocolloid element, at least one segment of perforated polymeric film being associated to the composite layer applied to the first area, comprising at least one layer of permeable polymeric film facing the skin of the user.

Further, the objectives of the present invention are achieved by means of an adhesive bandage, particularly for use on the skin, comprising a polymeric film that has a first surface facing the skin of the user and a second opposite surface, the first surface defining a first surface area that receives the application of at least one first composite layer formed by at least one adhesive element and at least one hydrocolloid element, at least one segment of perforated polymeric film being associated to the composite layer applied to the first area, which does not adhere to the skin of the user, thereby preventing maceration or re-injury of the wound upon removal of the bandage.

Further, the objectives of the present invention are achieved by means of an adhesive bandage, particularly for use on the skin, comprising a polymeric film that has a first surface facing the skin of the user and a second opposite surface, the first surface defining a first surface area that receives the application of at least one first composite layer formed by at least one adhesive element and at least one hydrocolloid element, at least one segment of perforated polymeric film being associated to the composite layer applied to the first area, comprising at least one composite layer facing the skin of the user.

According to another embodiment of the present invention the adhesive bandages are characterized in that at least one second composite layer formed by at least one adhesive element and at least one hydrocolloidal element is associated to the layer of polymeric film of the segment of polymeric film. According to another embodiment an adhesive bandage is provided wherein the segment of perforated polymeric film is associated to the polymeric film by associating the second composite layer of the segment with the first composite layer of the film. According to another embodiment a bandage is provided wherein at least one layer of polymeric film of the segment of polymeric film is associated to the second composite layer, which is formed by at least one adhesive element and at least one hydro colloidal element. With such a bandage it can also be provided that the segment of perforated polymeric film is associated to the polymeric film by associating the layer of polymeric film with the first composite layer of the film.

The present invention provides for an adhesive bandage, particularly for use over the skin, comprising a support layer, which has a first surface (S1) facing the skin of the user and a second opposite surface (S2), the first surface (S1) defining a first surface area that receives at least partially an application of at least one first composite layer, the bandage being characterized in that at least one segment of at least one double or multi-layer system is associated to at least a section of the composite layer wherein the double or multi-layer system comprises at least one permeable layer and at least one second composite layer and wherein the at least one segment of the double or multi-layer system is associated to the first composite layer via its second composite layer and/or wherein the at least one segment of the double or multi-layer system is associated to the first composite layer via its permeable layer.

In a preferred embodiment the support layer comprises a polymeric film which in particular is impermeable to liquids, but permeable to gases. Preferably the first composite layer comprises at least one first adhesive element and at least one first hydrocolloidal element and/or wherein the second composite layer comprises at least one second adhesive element and at least one second hydrocolloidal element. In another preferred embodiment the first composite layer is composed of at least one adhesive element and at least one first hydrocolloidal element, and/or the second composite layer is composed of at least one second adhesive element and at least one second hydrocolloidal element. It is possible but not necessary to employ identical first and second composite layers, or first and second composite layers at least the first and second adhesive elements or the first and second hydrocolloidal elements of which are essentially identical. In case the multi-layer system comprises one second composite layer and one permeable layer it is generally referred to as double layer system. According to one embodiment the permeable layer of said double or multi-layer system comprises a perforated layer, for example perforated film.

According to a first embodiment of the present invention an adhesive bandage is provided wherein at least one segment of the double or multi-layer system is associated to the first composite layer via its second composite layer. In this regard, the second composite layer preferably is associated to a section of the first composite layer and the permeable layer is associated to the second composite layer.

According to a second embodiment of the present invention an adhesive bandage is provided wherein at least one segment of the double or multi-layer system is associated to the first composite layer via its permeable layer. In this regard, the permeable layer preferably is associated to a section of the first composite layer and the second composite layer is associated to the permeable layer.

According to a third embodiment of the present invention an adhesive bandage is provided wherein at least a first segment of the double or multi-layer system is associated to the first composite layer via its second composite layer and wherein at least one second segment of the double or multi-layer system is associated to the first composite layer via its permeable layer.

According to another preferred embodiment the adhesive bandage according to the present invention is characterized in that the segment of the double or multi-layered system being associated to the first composite layer and having a second surface area is smaller than the first surface area.

Suitable hydrocollodial elements of the first and/or second composite layer comprise carboxymethyl cellulose, pectin, xanthan gum, polysaccarides, alginates, chitosan, marine algae extract, polyaspartic acid, polyglutamic acid, hyaluronic acid or salts and derivatives as well as mixtures thereof. Suitable adhesive elements of the first and/or second composite layer comprise, for example, a pressure acrylic adhesive.

Furthermore, suitable support layer materials comprise polyolefins, polyurethanes, polyethylene vinyl acetate, non-wovens, rubber materials, textiles or mixtures thereof.

Particular preferred adhesive bandages according to the present invention also include those wherein at least one permeable layer and/or at least one second composite layer comprises at least one, in particular a plurality of through bores, in particular through bores which are essentially perpendicular to the first surface (S1) of the support layer. In this context also those adhesive bandages are preferred wherein at least one through bore goes beyond said permeable layer and/or said second composite layer and reaches through at least part of the composite layer. It is particularly preferred that at least one, in particular a plurality of through bores of the permeable layer and the second composite layer are located in a matching position so that a contiguous passageway is generated. According to another preferred embodiment at least one through bore, in particular a plurality of through bores which reaches/reach through at least part of the composite layer is/are located in matching position with the through bore(s) of the permeable layer and the through bore(s) of the second composite layer thereby generating a contiguous passageway. These passageways are preferably essentially perpendicular to the first surface (S1).

According to another aspect of the present invention the underlying object has been solved by a process for the manufacture of an adhesive bandage according to the present invention, comprising the following steps:

(i) providing a support layer having a first surface (S1) and an opposite second surface (S2),
(ii) applying at least one first composite layer to at least part of the first surface (S1) of said support layer,
(iii) providing at least one permeable layer,
(iv) applying at least one second composite layer to the permeable layer, to form a double or multi-layer system, and
(v) associating at least a section of the double or multi-layer system to the first composite layer via the permeable layer and/or associating at least a section of the double or multi-layer system to the first composite layer via the second composite layer.

A preferred process further comprises the step of shaping the double or multi-layer system obtained in step (iv), in particular so that it covers an area smaller than the area covered by the support layer.

In a preferred embodiment the steps (i) and (iii) and/or (ii) and (iv) take place either concomitantly or at separate moments. The process of the present invention preferably further comprises providing at least one through bore, in particular a plurality of through bores, through the permeable layer and/or the second composite layer.

Finally, the objectives of the present invention are achieved by means of a process for manufacturing an adhesive bandage, particularly an adhesive bandage as defined in the two preceding paragraphs, comprising the following steps: (i) preparing and cutting the polymeric film; (ii) applying at least one first composite layer to a first surface of the polymeric film; (iii) preparing and cutting a layer of polymeric film; (iv) applying at least one second composite layer to the perforated polymeric film, shaping the perforated polymeric segment; (v) associating the perforated polymeric segment to the first composite later of the polymeric film; and (vi) making a plurality of through bores.

BRIEF DESCRIPTION OF THE DRAWINGS

The present invention will now be described in greater detail with reference to an embodiment represented in the drawings. The figures show.

FIG. 5 corresponds to a schematic sectional view of a second embodiment of the bandage illustrated in FIG. 3, and where its thickness is quite highlighted;

FIG. 6 is a schematic perspective view of a conventional adhesive bandage with an absorbent pad; and FIG. 7 corresponds to a schematic sectional view of the conventional adhesive bandage illustrated in FIG. 5.

DETAILED DESCRIPTION OF THE FIGURES

Figure 1:
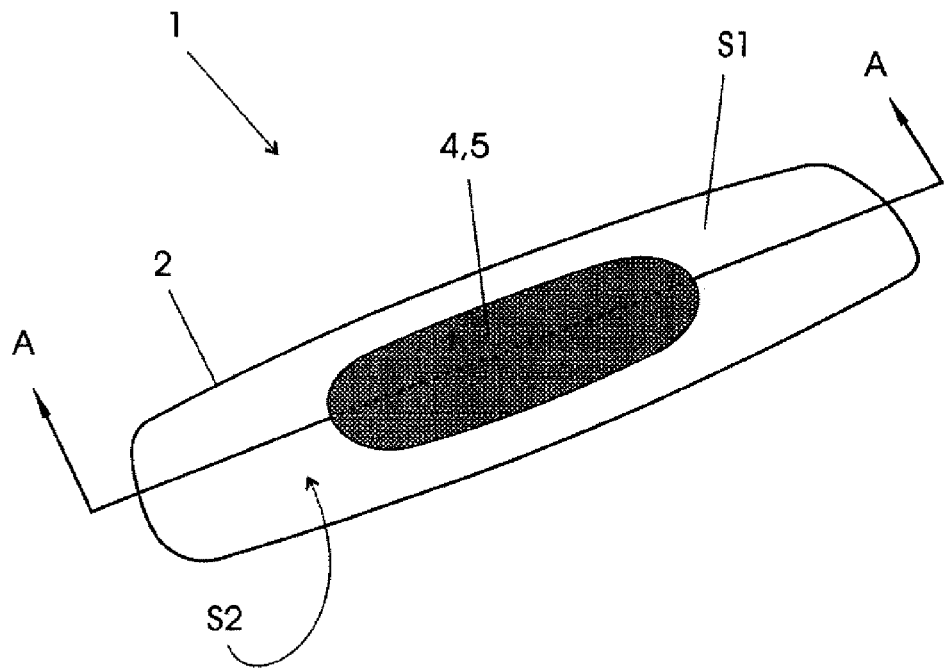
FIG. 1 is a schematic perspective view of a first embodiment of the adhesive bandage of the present invention.
Figure 2:
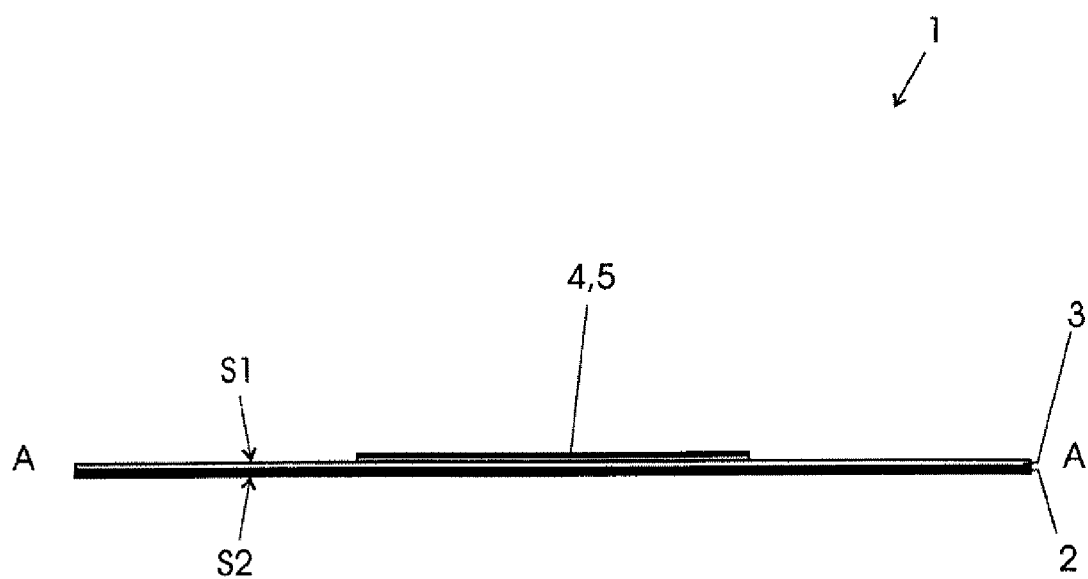
FIG. 2 corresponds to a schematic sectional view of the adhesive bandage illustrated in FIG. 1.
Figure 3:
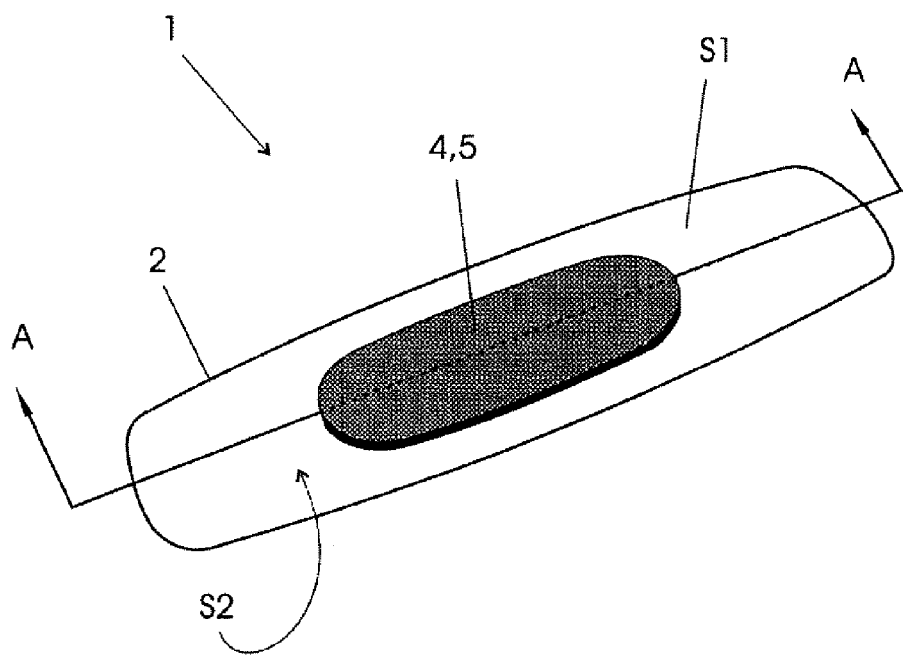
FIG. 3 is a schematic perspective view of the bandage illustrated in FIG. 1 with the thickness of the central portion quite highlighted.
Figure 4:
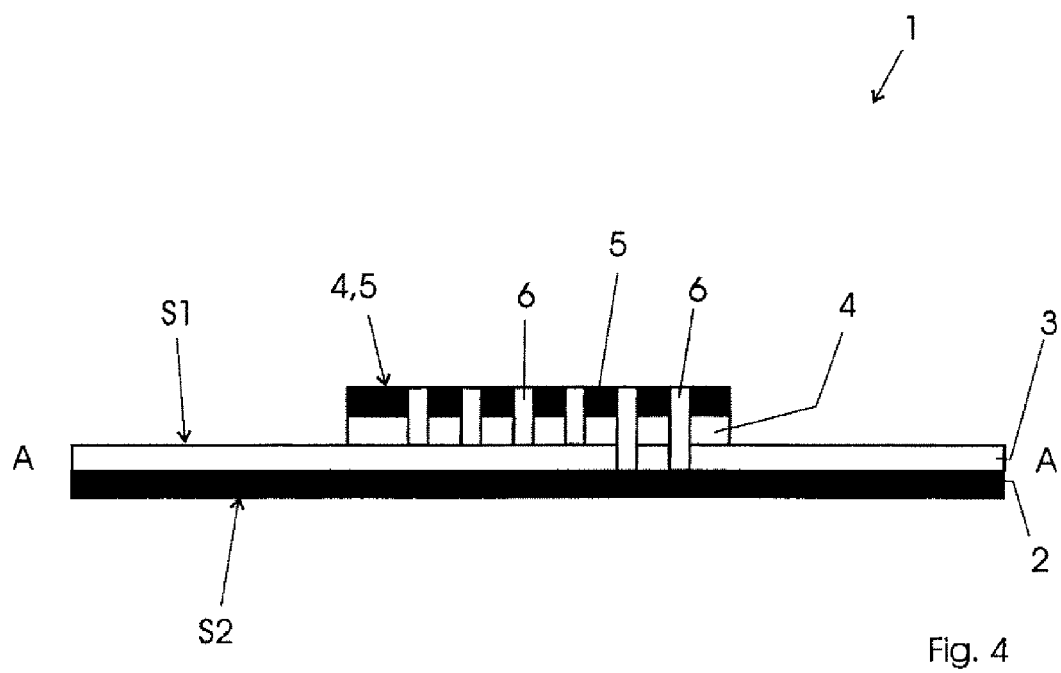
FIG. 4 corresponds to a schematic sectional view of the bandage illustrated in FIG. 3, and where its thickness is quite highlighted.

FIGS. 1 to 5 illustrate two possible embodiments of the adhesive bandage 1 of the present invention, while FIGS. 6 and 7 illustrate a conventional prior-art bandage 100 provided with an absorbent pad 200.

The conventional bandage 100 illustrated in FIGS. 6 and 7 comprises a main impermeable plastic film, to which quite thick absorbent pad 202 is associated, preferably by means of glue. The region dominated by the pad 200 does not contain any kind of adhesive, since it should not at all adhere to the wound, at the risk of causing additional injuries when the adhesive bandage 100 is removed from the skin (re-injury).

This type of conventional adhesive bandage 100, although efficient with regard to the capability of absorbing body exudates from the healing wound, due to the fact that the absorbent pad 200 is quite thick, exhibit little flexibility and ends up detaching from the skin of the user long before saturation, thus requiring an early replacement. Moreover, this type of bandage is not efficient in use as a skin protector or as breast protector or as a sanitary napkin.

Another type of bandage used is the one made from single-layer film without any absorbent pad, which is not illustrated in the figures because of its simplicity. By virtue of the characteristics of the component materials and to its reduced thickness, the single-layer adhesive bandage is highly flexible and so it can remain adhered to the skin for a long time, even if positioned in body-articulation regions. With a view to guarantee the absorption of body fluids, at least one hydrocolloid element mixed with the adhesive is applied.

By virtue of its high flexibility, this type of bandage remains in use without detaching until the hydrocolloid becomes saturated, and then it is replaced. Optionally, this type of adhesive bandage may also be configured so as to mask, as much as possible, its existence (presenting a finish of the sake color as the skin, frosted translucent, etc.).

The great disadvantage of this type of bandage lies in that fact that the mixture of adhesive and hydrocolloid is applied throughout its extent, and this is necessary above all in the region that covers the wound, since it is there that the presence of the hydrocolloid with its absorption capacity is crucial. However, since the hydrocolloid is associated with the adhesive, the wound region may undergo re-injury upon removal of the bandage.

The first configuration of the adhesive bandage 1 of the present invention, illustrated in FIGS. 1 to 4, in turn, does not have this drawback. It comprises at least one polymeric film 2, called also support layer, to which at least one first layer 3 composed of at least one adhesive element and at least one hydrocolloid element is associated.

The first support layer 2 may be of various shapes, as required (rectangular, circular, oblong, etc.), and its shape will that presented by the adhesive bandage 1, that is to say, the shape of the adhesive bandage is defined by the first support layer 2. Likewise, the composition of the first support layer 2 may vary, but it is preferably manufactured from a polyolefin film, polyurethane polymer, polyethylene, polyethylene vinyl acetate, polyurethane foam, and may still be made from a textile, non-woven material, rubber, etc.

The polymeric film or support layer 2 has a first surface S1 facing the skin of the user and a second opposite surface S2. The first surface S1 defines or has an area value called first surface area. The first layer (3) composed of adhesive and hydrocolloid is applied over the whole surface area defined by the first surface S1 (therefore, obviously facing the skin of the user).

Further preferably, the first support layer 2 is impermeable to liquids, but permeable to gases, which allows the injury and the skin to which the adhesive bandage 1 is adhered to breathe. In order for this to be possible, the support layer or the polymer comprises pores sized so as to allow only gases to pass, which are composed of molecules known to be small. Finally, one may conceive a layer 2 that is perforated in the regions that will not come in contact with the injury, further increasing skin ventilation. Alternatively, the first support layer 2 may further be totally impermeable to gases, when necessary.

The first composite layer 3, in turn, comprises at least one discreet hydrocolloid element. By "discreet elements" one understands particles of reduced size dispersed in the adhesive, as taught in U.S. Pat. Nos. 5,643,187 and 6,558,792, incorporated herein by reference. The hydrocolloid element used may be any substance that has a good performance in this use, as for example, sodium carboxymethyl cellulose, pectin, xanthan gum, polysaccharides, sodium or calcium alginates, chitosan, marine algae extract/(carrageenan), polyaspartic acid, polyglutamic acid, hyaluronic acid or salts and derivatives thereof, among others.

Hydrocolloids, such as sodium carboxymethyl cellulose and pectin, among others, are agents that form gels as soon as they come into contact with the body fluids emanated from injuries. In the use of adhesive bandages, these hydrocolloids are combined with elastomers and/or adhesives (the composition of which will be mentioned later). Preferably, the adhesive bandage 1 should guarantee a moistened environment, but without saturation, for healing, a situation favorable to the acceleration thereof.

Pectin is a complex-structure polysaccharide extracted from plant species (such as citric-fruit barks and apple pulp), which has a highly hydrophilic structure and, consequently, associates easily with the water molecules of body fluids emanated through the wound, forming a viscous gel in the injury bed. Its chemical similarity with alginates causes the physical properties of absorption and formation of gel to resemble each other.

Caraboxymethyl cellulose, in turn, is a cellulose derivative formed by reaction of cellulose with alkalis (such as sodium, potassium, calcium hydroxide, etc) and chloroacetic acid. It is the nature of the combined alkali that differentiates the ionic characteristic of carboxymethyl cellulose (when using sodium hydroxide, sodium carboxymethyl cellulose is formed). Like what occurs with pectin, carboxymethyl cellulose dissolves rapidly in the water of the fluids emanated through the wound, forming a gel in the wound with controlled viscosity.

As an additional advantage of the use of hydrocolloids, one should note that both pectin and carboxymethyl cellulose form a gel of acidic characteristics (pH of about 4), functioning as an antibacterial agent.

Prior to use of the adhesive bandage 1, hydrocolloid is substantially inert to water vapor, but as soon the gelling process begins, the adhesive bandage 1 becomes progressively more permeable. The gelling process continues, as long as the wound continues to release body fluids, until the hydrocolloid is used, and then the adhesive bandage 1 reaches saturation and should be replaced.

In the same way, the adhesive element used may be any one, as for example pressure acrylic adhesive, among others. Additionally, such an adhesive may contain a resin for increasing adhesion, a cohesion increasing agent, an absorbing agent (preferably a polyacrylate super-absorbent, a polyacrylate-salt super-absorbent or mixture thereof), a plasticizer and optionally a pigment. The first composite layer 3 may further be configured in discontinuous patterns, exhibiting an arrangement in lines, web, spray or any other that a parson skilled in the art considers to be continuous.

At least one segment of perforated polymeric film 4,5 is associated to the first layer 3, which has a second surface substantially smaller than the first one (the surface area defined by the first surface S1 of the support layer 2).

The segment of perforated polymeric film 4,5 is preferably but not compulsorily positioned centralized with respect to the support layer 2 and, as will be discussed in detail later, it has the function of acting over the injury on the skin of the user, preventing re-injury and keeping good properties as far as maceration is concerned.

In order to perform this function, the segment of perforated polymeric film 4,5 comprises at least one layer of permeable polymeric film 5, to which one associates at least one second composite layer 4 formed by at least one adhesive element and at least one hydro colloidal element.

By preference, the permeable layer 5 is similar in constitution to the support layer 2 and the second composite layer 4 is similar to the first composite layer 3, for the sake of manufacturing ease, but it is evident that both of them may have any necessary or desirable constitutions, provided that they are functional.

In this first configuration of the bandage illustrated in FIGS. 1 to 4, the association of the segment of perforated polymeric film 4,5 to the support layer 2 is effected by associating the second composite layer 4 to the first composite layer 3. Therefore, it is the permeable layer 5 that remains facing the skin of the user when the bandage is ready to be used, and this is advantageous, since no adhesive is applied to the user-facing surface of this layer 5.

The second configuration of the bandage of the present invention, illustrated in FIG. 5, is identical to the first one in almost all aspect, with the exception of the fact that the segment of polymeric film is mounted inverted, that is to say, the permeable layer 5 of the segment 4, 5 is associated to the first composite layer 3 and the second composite layer 4 faces the skin of the user. This constitution brings some differences to the performance of the bandage, which make it suitable for some uses and will be described later.

With a view to protect the bandage 1 until it is applied, one preferably provides a sheet of non-stick material (not shown) having a shape analogous to that of the support layer or the like, which remains positioned in contact with the first composite layer 3 and (i) with the permeable layer 5 (with the latter in the region where the segment of perforated film is associated to the support layer 2) in the case of the first embodiment of the bandage or (ii) with the second composite layer 4 (also in the region where the segment of perforated film is associated to the support layer 2) in the case of the second embodiment of the bandage.

Thus, one preserves (i) the adhesion capability of the first composite layer 3, (ii) the hydrocolloidal properties, and (iii) the hygiene of the permeable layer 5 or of the second composite layer 4 (depending on the configuration of the bandage), which will be in contact with the injury.

The segment of permeable polymeric film 4,5 comprises a plurality of substantially perpendicular through bores 6 that passes through both the polymeric film 5 (making it permeable) and the second composite layer 4. Preferably, at least one of the through bores 6 goes beyond the polymeric film layer 5 and the second composite layer 4, and even reach the first composite layer 3. In the two situations mentioned the bores 6 can be seen in schematic enlargements in FIGS. 4 and 5, since the diameter is very reduced and the their length is even smaller.

The through bores 6 correspond to real channels for carrying body fluids, enabling them to be conducted by capillarity away from the discharge region (the skin injury) and to be absorbed by the hydro colloidal elements. For this reason it is preferable that the segment of permeable polymeric film 4, 5 should comprise the second composite layer 4, which increases the amount of hydrocolloid and, by inference, the absorption capacity of the bandage 1.

For use of the first embodiment of the bandage 1, the user, after removing the sheet of non-stick material, should position it in such a way that the polymeric film layer 5 will be positioned over the injury, preventing the first composite layer 3 from being thus positioned. Since there is no adhesive on the surface of the polymeric film layer 5 facing the user, there is no risk that the portion will stick to the injury, causing re-injury upon removal of the bandage 1.

After positioning the bandage 1, the body liquids emanated from the injury pass through the bores 6 and through the polymeric film layer 5 (which, with the exception of the bores 6, is impermeable), reaching the second composite layer 4. At this moment, the liquids begin to react with the hydrocolloid, remaining stored. The bores 6 further conduct the liquids as far as the first composite layer, which is larger in area, where the large amount of hydro colloidal material changes into a great absorption capacity.

Since there is no adhesive on the surface of the polymeric film layer 5 facing the user, there is no risk that this portion sticks to the wound, causing re-injury upon removal of the bandage 1.

On the other hand, for use of the second embodiment of the bandage 1, the user removes the sheet of non-stick material and positions the bandage in such a way that the second composite layer 4 will be positioned over the injury. In this second embodiment, since the second composite layer 4 comprises a mixture of adhesive and hydrocolloid, the risk of re-injury is not so low, but on the other hand the absorption capacity is maximized, since the hydrocolloid remains in direct contact with the injury.

The second embodiment of the bandage is more suitable, for instance, for use in dressings where one desires higher velocities and absorption capacity, a situation where the saturation of the bandage occurs more rapidly. In this regard, one should further mention that, upon saturation of the hydrocolloid present in the second composite layer 4, there is natural displacement thereof, which attenuates the possibility of re-injury. In this second embodiment, the bores 6 act as described before.

It is important to note that the segment of permeable polymeric film 4,5 positioned over the first composite layer 3 brings an extremely reduced increase in the thickness of the bandage 1, since its thickness is the same (or almost the same) as that of the bandage prior to application. Besides, this extremely reduced increase in the thickness will occur only in the region where this segment is applied. The bandage 1 then has a thickness as reduced as that of bandages made from a single-layer film of the prior art, with the great advantage of reducing to virtually zero the chances of re-injury/maceration.

Thus, with the present bandage 1, it is possible to obtain the advantages of the reduced thickness of the monolayers bandages together with the capability to prevent re-injury of bandages with pads, and a capability of sufficient absorption due to the existence of the hydrocolloid element in the first and second composed layers 3,4.

In addition to the above example, the adhesive bandage 1 of the present invention can be used, for instance, as a breast protection. To this end, it is enough to handle adequately the variables such as areas of the support layer 2 and of the segment of permeable polymeric film 4,5.

It is further possible for the bandage to be one of the components of a breast protector or an absorbent composed of further elements and layers, so that the absorption desired will be achieved.

Finally, the process for manufacturing the adhesive bandage of the present invention is per se a novel and innovatory invention. Essentially, in one embodiment the process comprises the following steps:

(i) preparing and cutting the polymeric film 2;
(ii) applying at least one first composite layer 3 to a first surface S1 of the polymeric film 2;
(iii) preparing and cutting a layer of polymeric film 5;
(iv) applying at least one second composite layer 4 to the layer of perforated polymeric film 5, shaping the perforated polymeric segment 4,5;
(v) associating the perforated polymeric segment 4,5 to the first composite layer 3 of the polymeric film 2; and
(vi) making a plurality of through bores 6.

Evidently, the steps (i) and (iii) of preparing and cutting the polymeric layer 2 and of the layer of polymeric film 5, respectively, may occur either concomitantly or at separate moments, since this makes no difference to the effect of protecting the invention. In the same way, this may happen with the steps (ii) and (iv).

Preferably, the step (vi) of making the through bores 6 is carried out at the end, but nothing prevents one from making these bores before, as for instance at the time of applying the first and the second composite layers 3,4 (steps ii and iv), or still at another time.

A preferred embodiment having been described, one should understand that the scope of the present invention embraces other possible variations, being limited only by the contents of the accompanying claims, which include the possible equivalents.

I claim:

1. An adhesive bandage, comprising:
    a support layer having a first surface facing skin of a user and a second opposite surface, the first surface defining a first surface area,
    a first composite layer applied at least partially to the first surface area, the first composite layer comprising an adhesive element,
    at least one segment of at least one multi-layer system associated to at least a section of the first composite layer, wherein the multi-layer system comprises at least one perforated permeable polymeric film layer comprising a plurality of through bores which are essentially perpendicular to the first surface of the support layer and at least one second composite layer comprising a hydrocolloidal element and an adhesive element.

2. The adhesive bandage according to claim 1 wherein the multi-layer system is associated to the first composite layer via the second composite layer 3. The adhesive bandage according to claim 1 wherein the multi-layer system is associated to the first composite layer via the perforated permeable polymeric film layer.

4. The adhesive bandage according to claim 1 wherein the second composite layer comprises a plurality of through bores which are essentially perpendicular to the first surface of the support layer.

5. The adhesive bandage according to claim 4 wherein at least one of the plurality of through bores goes beyond the perforated permeable polymeric film layer and the second composite layer to reach the first composite layer.

6. The adhesive bandage according to claim 1 wherein the first composite layer further comprises at least one hydrocolloidal element.

7. The adhesive bandage according to claim 1 wherein the segment of the multi-layer system associated to the first composite layer has a second surface area smaller than the first surface area of the support layer.

8. The adhesive bandage according to claim 1 further comprising at least one sheet of non-stick material having a shape analogous to that of the support layer, which is releasably associated to that side of the bandage applied to a surface which is opposite the second surface of the support layer.

9. The adhesive bandage according to claim 1 wherein the first composite layer is discontinuous.

* * * * *